(12) United States Patent
Ootsubo

(10) Patent No.: US 8,382,752 B2
(45) Date of Patent: Feb. 26, 2013

(54) MEDICAL DEVICE

(75) Inventor: Seiichi Ootsubo, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1253 days.

(21) Appl. No.: 12/143,636

(22) Filed: Jun. 20, 2008

(65) Prior Publication Data

US 2009/0005776 A1    Jan. 1, 2009

(30) Foreign Application Priority Data

Jun. 25, 2007  (JP) ................................ 2007-166773
Jun. 25, 2007  (JP) ................................ 2007-166792

(51) Int. Cl.
*A61B 18/18* (2006.01)

(52) U.S. Cl. ......................................................... 606/41

(58) Field of Classification Search ..................... 606/41
See application file for complete search history.

(56) References Cited

U.S. PATENT DOCUMENTS

| | | | |
|---|---|---|---|
| 5,507,744 A | 4/1996 | Tay et al. |
| 5,709,224 A | 1/1998 | Behl et al. |
| 5,810,810 A | 9/1998 | Tay et al. |
| 5,827,268 A | 10/1998 | Laufer |
| 5,919,200 A | 7/1999 | Stambaugh et al. |
| 6,004,316 A | 12/1999 | Laufer |
| 6,063,085 A | 5/2000 | Tay et al. |
| 6,077,261 A | 6/2000 | Behl et al. |
| 6,629,534 B1 | 10/2003 | St. Goar et al. |
| 6,752,813 B2 | 6/2004 | Goldfarb et al. |
| 6,939,348 B2 | 9/2005 | Malecki et al. |
| 7,165,552 B2 | 1/2007 | Deem et al. |
| 7,186,251 B2 | 3/2007 | Malecki et al. |
| 7,226,467 B2 | 6/2007 | Lucatero et al. |
| 7,257,450 B2 | 8/2007 | Auth et al. |
| 7,293,562 B2 | 11/2007 | Malecki et al. |
| 7,311,701 B2 | 12/2007 | Gifford et al. |
| 2004/0003819 A1 | 1/2004 | St. Goar et al. |
| 2004/0030382 A1 | 2/2004 | St. Goar et al. |
| 2004/0039442 A1 | 2/2004 | St. Goar et al. |

(Continued)

FOREIGN PATENT DOCUMENTS

WO    WO 99/18871 A1    4/1999
WO    WO 2004/086944 A2   10/2004

(Continued)

OTHER PUBLICATIONS

Extended European Search Report issued in corres. EP 08 15 8594, Dec. 5, 2008, European Patent Office, Munich, DE.

(Continued)

*Primary Examiner* — Nicholas Lucchesi
*Assistant Examiner* — Jenna Zhang
(74) *Attorney, Agent, or Firm* — Buchanan Ingersoll & Rooney PC

(57) ABSTRACT

A medical device for fusing or necrosing a biological tissue, including a first electrode member and a second electrode member protruded from a non-electrically-conductive attachment portion configured to sandwich the biological tissue; and an energy supply unit configured to supply electric energy to between the first electrode member and the second electrode member, wherein the region of a predetermined length in a direction of axial line from the attachment portion in at least one of the electrode members within the first electrode member and the second electrode member is coated with an electrical insulator.

15 Claims, 8 Drawing Sheets

U.S. PATENT DOCUMENTS

| | | |
|---|---|---|
| 2004/0044350 A1 | 3/2004 | Martin et al. |
| 2004/0049207 A1 | 3/2004 | Goldfarb et al. |
| 2004/0092962 A1 | 5/2004 | Thornton et al. |
| 2004/0225300 A1 | 11/2004 | Goldfarb et al. |
| 2004/0243122 A1 | 12/2004 | Auth et al. |
| 2004/0267191 A1 | 12/2004 | Gifford, III et al. |
| 2005/0021056 A1 | 1/2005 | St. Goar et al. |
| 2005/0021057 A1 | 1/2005 | St. Goar et al. |
| 2005/0033288 A1 | 2/2005 | Auth et al. |
| 2005/0033446 A1 | 2/2005 | Deem et al. |
| 2005/0080406 A1 | 4/2005 | Malecki et al. |
| 2005/0131401 A1 | 6/2005 | Malecki et al. |
| 2005/0131460 A1 | 6/2005 | Gifford, III et al. |
| 2005/0192626 A1 | 9/2005 | Widomski et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2006/0020275 A1 | 1/2006 | Goldfarb et al. |
| 2006/0027241 A1 | 2/2006 | Malecki et al. |
| 2006/0074410 A1 | 4/2006 | Malecki et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 * | 11/2006 | Francis et al. ............ 606/27 |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |
| 2007/0027445 A1 | 2/2007 | Gifford et al. |
| 2007/0038293 A1 | 2/2007 | St.Goar et al. |
| 2007/0044811 A1 | 3/2007 | Deem et al. |
| 2007/0078485 A1 | 4/2007 | Deem et al. |
| 2007/0088355 A9 | 4/2007 | Auth et al. |
| 2007/0093804 A1 | 4/2007 | Kaveckis et al. |
| 2007/0093805 A1 | 4/2007 | Auth et al. |
| 2007/0100324 A1 | 5/2007 | Tempel et al. |
| 2007/0100356 A1 | 5/2007 | Lucatero et al. |
| 2007/0106214 A1 | 5/2007 | Gray et al. |
| 2007/0112347 A1 | 5/2007 | Malecki et al. |
| 2007/0118155 A1 | 5/2007 | Goldfarb et al. |
| 2007/0123824 A1 | 5/2007 | Kaveckis |
| 2007/0123851 A1 | 5/2007 | Alejandro et al. |
| 2007/0123852 A1 | 5/2007 | Deem et al. |
| 2007/0129737 A1 | 6/2007 | Goldfarb et al. |
| 2007/0203479 A1 | 8/2007 | Auth et al. |
| 2007/0287999 A1 | 12/2007 | Malecki et al. |
| 2007/0299434 A1 | 12/2007 | Malecki et al. |
| 2008/0004658 A1 | 1/2008 | Malecki et al. |
| 2008/0009859 A1 | 1/2008 | Auth et al. |
| 2008/0051703 A1 | 2/2008 | Thornton et al. |
| 2008/0051807 A1 | 2/2008 | St. Goar et al. |
| 2008/0058683 A1 | 3/2008 | Gifford et al. |
| 2008/0097489 A1 | 4/2008 | Goldfarb et al. |
| 2008/0140064 A1 | 6/2008 | Vegesna |
| 2008/0140068 A1 | 6/2008 | Taimisto |
| 2008/0140069 A1 | 6/2008 | Filloux et al. |
| 2008/0140070 A1 | 6/2008 | Filloux et al. |
| 2008/0140071 A1 | 6/2008 | Vegesna |
| 2008/0140074 A1 | 6/2008 | Horne et al. |
| 2008/0140112 A1 | 6/2008 | Horne |
| 2008/0140113 A1 | 6/2008 | Taimisto |
| 2008/0140170 A1 | 6/2008 | Filloux et al. |

FOREIGN PATENT DOCUMENTS

| | | |
|---|---|---|
| WO | WO 2006/127970 A2 | 11/2006 |
| WO | WO 2006127970 A2 * | 11/2006 |
| WO | WO 2007/038609 A2 | 4/2007 |
| WO | WO 2007/100067 A1 | 9/2007 |
| WO | WO 2008/073727 A1 | 6/2008 |

OTHER PUBLICATIONS

Partial European Search Report issued in corres. EP 08 15 8594, Oct. 27, 2008, European Patent Office, Munich, DE.

* cited by examiner ically the patent foramen ovale.

MEDICAL DEVICE

CROSS-REFERENCES TO RELATED APPLICATIONS

This application is based upon Japanese Patent Applications No. 2007-166773 and No. 2007-166792 filed Jun. 25, 2007 the contents of which are hereby incorporated by reference.

BACKGROUND OF THE INVENTION

1. Field of the Invention

The present invention relates to a medical device which closes a defect occurring in a living body and particularly to an improvement of electrode members sandwiching a biological tissue.

2. Description of the Related Art

Recently, a patent foramen ovale (hereinafter, referred as to PFO: Patent Foramen Ovale) has been cited for a cardiogenic factor of a stroke and a hemi headache. A PFO is a symptom in which a foramen ovale which makes blood shunt for the right to the left in the heart of a fetal period remains even if a fetus becomes adult and it is said that 20 to 30% of adults possess it.

The foramen ovale occurs at a septum secundum (Septum Secundum, hereinafter, referred to as atrial septum) of the heart and the pressure on the left atrium side exceeds the pressure on the right atrium side in the heart on a normal occasion, so that it is occluded by a septum primum (Septum Primum, hereinafter, referred to as foramen ovale valve), but when the pressure on the right atrium side exceeds the pressure on the left atrium side on a strain occasion (for example, when coughing, when holding on) or the like, the foramen ovale valve opens to the left atrium side and it happens that blood flows from the right atrium side (venous side) into the left atrium side (arterial side). When a thrombus is included in this blood, it happens that the thrombus is shifted from the venous side to the arterial side, flows in a route of left atrium →left ventricle→aorta→brain, and it becomes a factor for a stroke, hemi headache or the like.

For a treatment with respect to such a disease, a treatment by a percutaneous catheter procedure is considered to be a desirable method if the same effect as an open heart surgery can be obtained.

A device of a closing technique using the percutaneous catheter can be used also in case of closing defects such as a congenital atrial septum defect (ASD), a PFO, a ventricular septal defect (VSD) and a patent ductus arteriosus (PDA), and the conventional device is a device sandwiching the foramen ovale valve and the atrial septum by using disk-shaped membranes or anchor members for closing the defect and these are detained in the body.

The membranes or anchor members are foreign substances for a human body and moreover, a thrombus is easy to be attached. In particular, when a thrombus is attached on a disk-shaped membrane or the like on the left atrium side, this flows and there is a possibility that it becomes a cause of a stroke, and there is also a fear that a foramen ovale valve of a thin wall thickness is broken. In addition, these members are not position-fixed in a state of being sandwiched and there is also a possibility of causing a positional displacement.

Consequently, recently, there has been proposed a PFO closing device described in WO2004/086944 A2. This PFO closing device is an apparatus inserted into the foramen ovale from the right atrium toward the left atrium, a foramen ovale valve is pulled to the foramen ovale so as to close it and the tissue is to be inosculated by applying electric energy. However, the foramen ovale, the foramen ovale valve and the atrial septum are different not only in small/large sizes but also in a condition of thicknesses, shapes or the like depending on persons and according to circumstances, it happens that the size or the like of the apparatus is restricted a lot. Also, even on an occasion when the procedure is performed, there is a fear that it becomes difficult to pull various forms of foramen ovale valves to the foramen ovale at anytime and certainly.

Consequently, it is also possible to suture the tissue by sandwiching the foramen ovale valve and the atrial septum using a pair of electrodes and by applying electric energy from both the electrodes. However, when electric energy is applied to the biological tissue in the blood in a state in which the electrode is exposed, a thrombus is generated at the periphery of the electrode depending on circumstances. In particular, it sometimes happens that the biological tissue is contracted by receiving thermal influence. When the biological tissue is thermally contracted, there is also a fear that the proximal side of the electrode member contacting with the biological tissue is exposed and a thrombus will attach on this exposed portion.

SUMMARY OF THE INVENTION

The object of the present invention is to eliminate the problem mentioned above and provides a medical device in which it is hard for the thrombus to be attached to the electrode even if the electric energy is applied in the blood and it is possible to perform a procedure for fusing or necrosing the tissue safely and certainly.

The object mentioned above is accomplished by a medical device for fusing or necrosing a biological tissue, including a first electrode member and a second electrode member protruded from a non-electrically-conductive attachment portion configured to sandwich the biological tissue; and an energy supply unit configured to supply electric energy to between the first electrode member and the second electrode member, wherein the region of a predetermined length in a direction of axial line from the attachment portion in at least one of the electrode members within the first electrode member and the second electrode member is coated with an electrical insulator.

According to the present invention, the region of a predetermined length in the direction of axial line from the attachment portion of at least one of the electrode members is coated with the electrical insulator, so that when a procedure supplying the electric energy to the biological tissue is performed, even if the biological tissue is thermally contracted slightly, it does not happen that a portion of the electrode members is exposed in the blood, and it is possible to prevent occurrence of such a problem that a thrombus will be attached by coagulating the blood which flows in the periphery of the electrode members.

It is preferable that the region is coated with an electrical insulator is configured to be a region in which contraction of the biological tissue is completed by the electric energy supply. As doing in this manner, it does not happen that the electrode members are exposed in the blood along with thermal contraction of the biological tissue until the procedure is completed, and the procedure for fusion or necrosis or the like of the tissue can be carry out easily while preventing attachment of a thrombus certainly.

In case the coat region of the electrical insulator is configured to be 0.5 mm to 10 mm, it is possible to make it a medical device which is possible to perform the procedure for fusion or necrosis or the like of the tissue while preventing attachment of a thrombus with respect to the most portion of the procedure.

In case a surface of the electrode member which is not coated with the electrical insulator is coated with an electrically-conductive material which is hard to be attached with a biological tissue, a thrombus or blood, attachment of a thrombus can be prevented much more.

In case a portion which is protruded from an attachment portion of at least one of the electrode members is constituted by a circular-shaped or a ring-shaped needle-shaped member for the section perpendicular to the axis, it is possible to stick it into the biological tissue in a case in which a defect of PFO or the like is closed, and in a stabilizingly dispose state in which a position of the one of the electrode members is fixed to the biological tissue, it is possible to perform the procedure of the sandwich of a biological tissue or the like and it is possible to attempt easiness, stability and speed-up of the procedure.

In case a portion which is protruded from the attachment portion of the other electrode member is a flat plate shape so as to face to one of the electrode member, in a case in which a biological tissue of a defect portion of the PFO or the like is sandwiched, it possible to sandwich it certainly, the electric energy supply is smooth and the procedure becomes easy.

The electrode member is constituted for a main body portion thereof of the electrode members by an electrically-conductive member and the circumferential surface thereof is coated with an electric insulator, and on the contrary, it is also allowed to be the main body portion which is constituted by an electric insulator and the circumferential surface thereof is coated with an electrically-conductive member. More specifically, a main body portion of at least one of electrode members is constituted by a synthetic resin and it is also allowed to provide an electrically-conductive film at a partial outside circumferential surface of the main body portion. As doing in this manner, even if the electrically-conductive film portion is temperature-increased by the electric energy supply, the heat of this electrically-conductive film is hard to be transmitted to a portion of the main body in which the electrically-conductive film is not provided, and even if this portion is contacted with the blood, a thrombus becomes hard to attach to here.

In case the main body is composed of a synthetic resin with electrical insulating properties having heat resistance, the heat and electricity are hard to be transmitted to a portion in which the electrically-conductive film is not provided and attachment prevention of the thrombus in here becomes more effective.

In case there is provided the electrically-conductive film so as to extend in a direction of axial line at the opposing surface sides of both the electrode members which are provided to face each other, it is possible to prevent temperature increase of the anti-electrically-conductive film side of the main body and to prevent attachment of a thrombus and attachment of tissues with respect to this portion.

In case the each electrode member is coated with the electrically-conductive film so as to make each surface area of the electrode surfaces differ mutually, it is possible to prevent temperature increase and attachment of a thrombus by depending on electric energy concentration to the electrode member of the one side, and easiness and smoothness of the procedure become possible.

In case the surface of the electrically-conductive film is coated with an electrically-conductive material which is not attached with a biological tissue, a thrombus or blood, it is possible to prevent attachment of a thrombus much more.

In case the area ratio (S1/S2) between the surface area (S2) of the electrode surface of the one of electrode members and the surface area (S1) of the electrode surface of the other electrode member is made to be more than 0.6 to less than 1.0, it becomes difficult for either one of the electrode members to be attached with a thrombus and the procedure becomes easier.

In case the attachment portion is constituted by a catheter provided in a guiding catheter, there must be housed in the catheter substantially only with both the electrode members or with these members and hold mechanism thereof, so that the constitution becomes very simple and it is possible to simplify the procedure more also in this point of view.

When a positioning mechanism for positioning the one electrode member at a predetermined position with respect to the foramen ovale is provided in this medical device, the sticking becomes accurate and certain when sticking to a tissue such as a foramen ovale valve or an atrial septum and the like is executed, and it is possible to make also the procedure of the inosculating operation more accurate, more speedy and also easier.

When there are provided in this medical device with a positioning hold mechanism composed of a positioning portion for positioning the one electrode member with respect to the foramen ovale and a holding portion for holding the foramen ovale valve with respect to the one electrode member so as not to allow the backward movement thereof, such operations referred to as positioning and holding the foramen ovale valve can be carried out in a lump and even in case of a thin-walled foramen ovale valve, the sticking is executed for a predetermined position without breaking or hurting that valve, so that safing and simplification of the procedure are improved considerably and it is possible to perform the procedure accurately and also speedily.

In case the energy supply unit is formed so as to control the electric current by the impedance of the biological tissue between both the electrode members, it can have correspondence easily in response to the state of the tissues of the foramen ovale valve and the atrial septum which differ depending on a person, and the safety and the convenience of the procedure are obtained.

DESCRIPTION OF THE PREFERRED EMBODIMENTS

Hereinafter, exemplified embodiments of the present invention will be explained in detail with reference to the drawings.

<First Embodiment>

Figure 1:
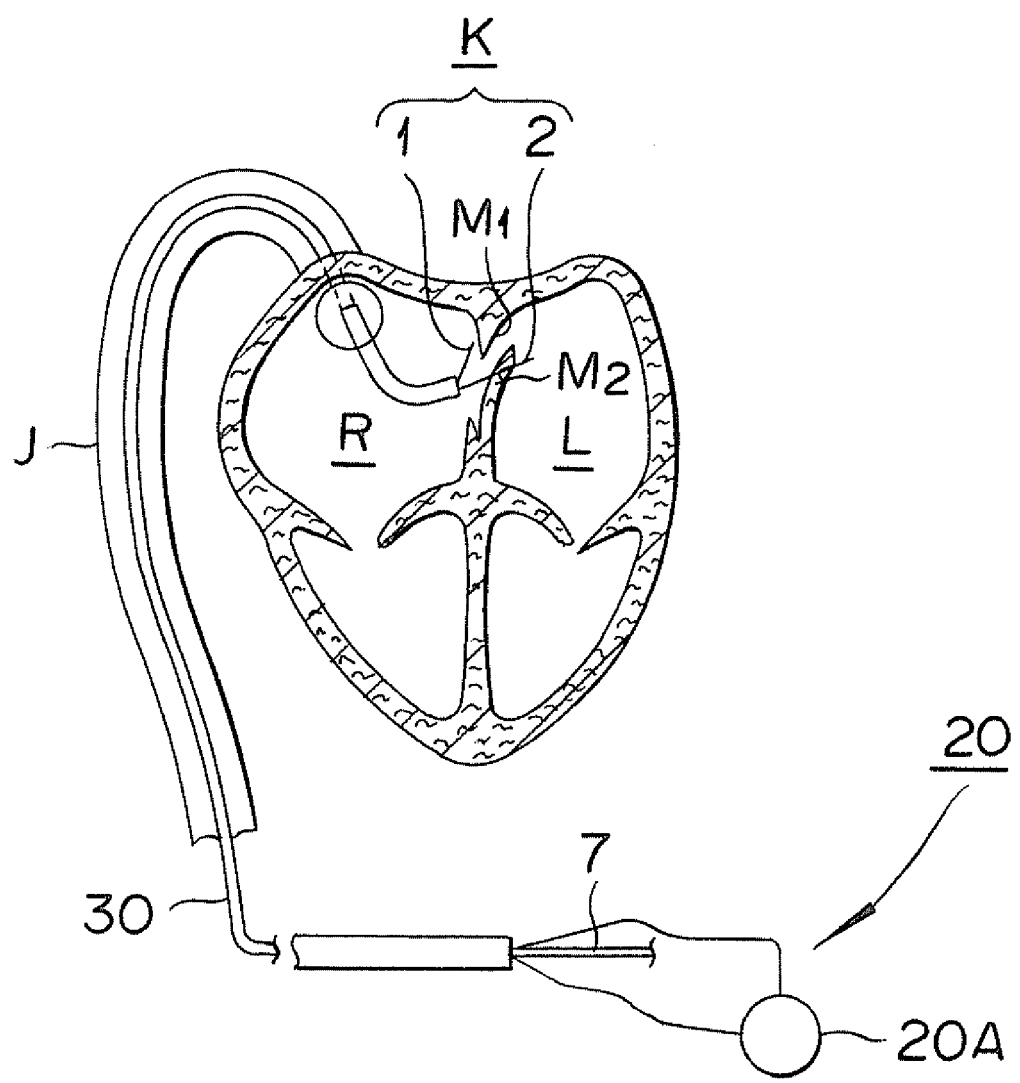
FIG. 1 is a schematic cross-section view showing a medical device according to the present invention.

First, it is outlined with respect to a medical device for PFO of the First embodiment. This medical device, as shown in FIG. 1, includes a clamper K (first electrode member 1 and second electrode member 2) which is installed in a percutaneous catheter 30, and in a state of sandwiching a foramen ovale valve M2 and an atrial septum M1 which are biological tissues M by means of the clamper K, electric energy from an energy supply unit 20 is supplied to the sandwiched foramen ovale valve M2 and atrial septum M1, wherein both of them are to be inosculated or fused.

It should be noted in the drawing that "J" denotes an inferior vena cave, "L" denotes a left atrium and "R" denotes a right atrium.

Figure 2:
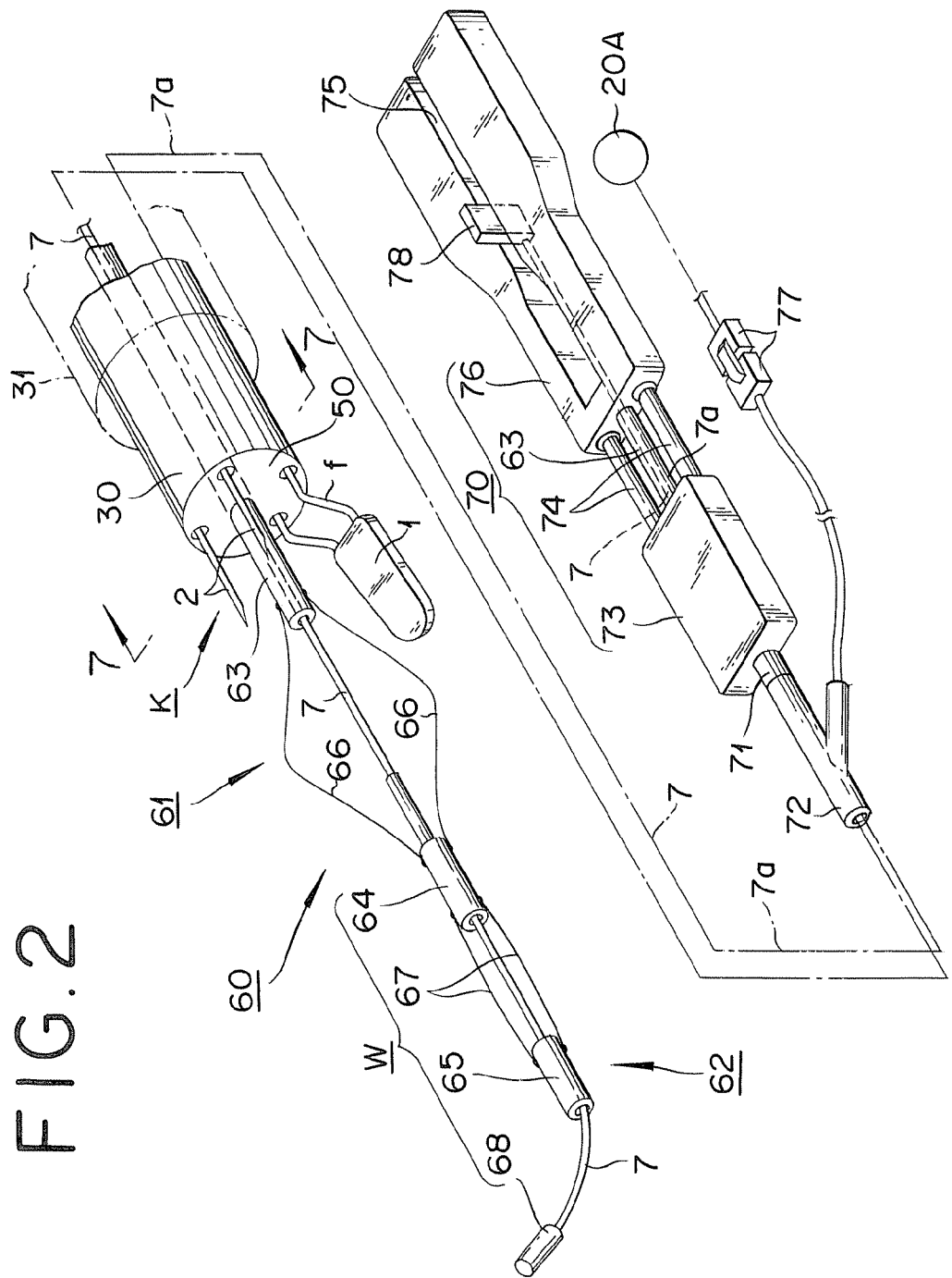
FIG. 2 is a perspective view showing the first embodiment of the present invention.

Specifically, the medical device is constituted as shown in FIG. 2. It should be noted in FIG. 2 that only an operation unit at hand 70 is demagnified because of space limitations.

The medical device includes an operation unit at hand 70 provided on the proximal side; a guiding catheter 31 mounted on the operation unit at hand 70 for the proximal side thereof; a catheter 30 provided in the guiding catheter 31, a positioning hold mechanism 60 provided at a distal portion of the catheter 30; a support body 50 provided position-fixedly at the distal portion in the inside of the catheter 30; and a clamper K provided in the support body 50. It should be noted in the following explanation that the side of the operation unit at hand of the medical device is referred to as "proximal side" and the side of the clamper K or the foramen ovale valve M2 is referred to as "distal side".

Figure 3:
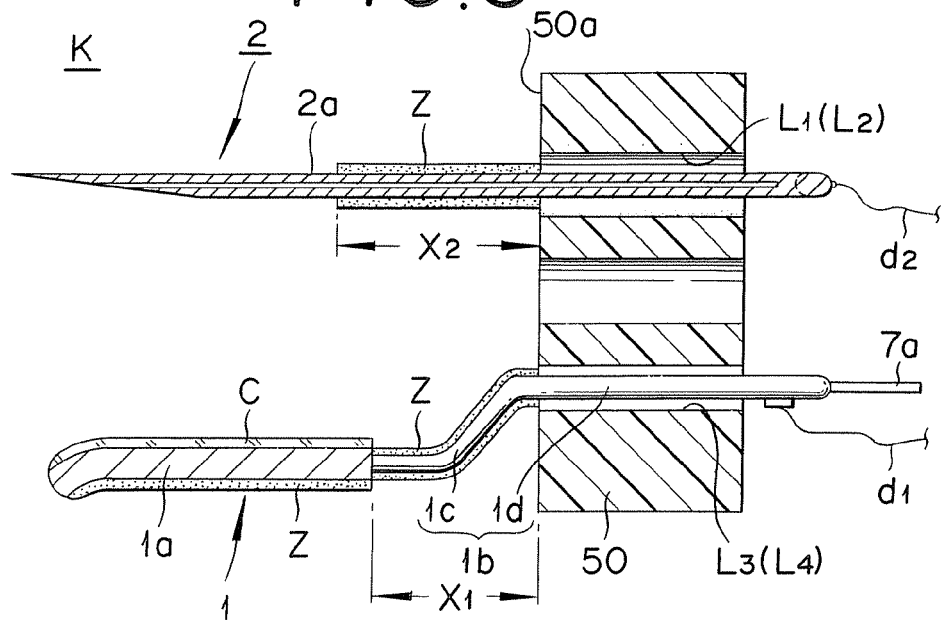
FIG. 3 is a cross-section view showing a clamper according to the first embodiment.
Figure 4:
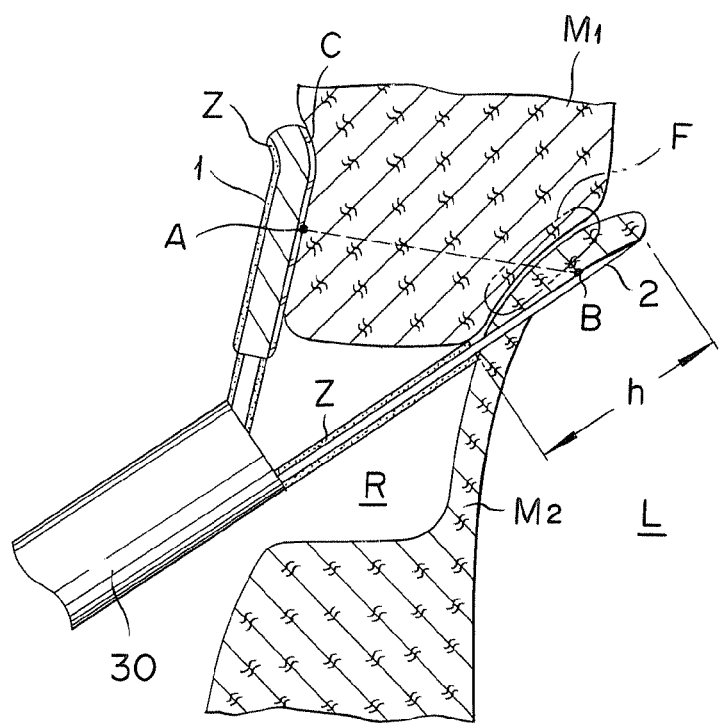
FIG. 4 is a schematic cross-section view showing a state in which a foramen ovale valve and an atrial septum are sandwiched by a pair of electrode members.

It will be described in more detail. First, the clamper K of the present embodiment is constituted by the first electrode member 1 and the second electrode member 2. As shown in FIG. 3, these electrode members 1, 2 are held at the support body 50 for the proximal portion thereof and are protruded from the support body 50 so as to face each other. As shown in FIG. 4, the first electrode member 1 disposed on the proximal portion is of contacting one side surface of the atrial septum M1 directly and the second electrode member 2 disposed on the distal side is of sticking in the foramen ovale valve M2.

The first electrode member 1 is constituted by a main body portion 1a formed in an electrically-conductive flat plate shape and a pair of wire portions 1b connected to the proximal portion. The wire portion 1b includes a bend portion 1c and a straight-shaped portion 1d, the straight-shaped portion 1d is inserted into lumens L3, L4 of the support body 50, and one piece of operation member 7a and a conductive wire d1 are provided on the proximal side thereof. Therefore, if the operation member 7a coupled to the first electrode member 1 is traction-operated, it is possible, when the bend portion 1c gets into the entrance portion of the lumens L3, L4 of the support body 50, to make the first electrode member 1 approach and separate with respect to the second electrode member 2 and it is possible to carry out the sandwich of the biological tissue by both the electrode members easily and smoothly even in a case of the distal portion of the fine catheter 31.

Here, it may be a SUS material for the material of the main body portion 1a, but it is preferable to use a material which does not exert bad influence to a living body such as, for example, gold, silver, platinum, tungsten, palladium or alloys of these, Ni—Ti alloy, titanium alloy or the like.

The first electrode member 1 is constituted by a flat plate-shaped electrode member, so that the contact area with the biological tissue can be secured and also, even if the second electrode member 2 is made to be a needle-shaped electrode member, which will be described later, the sandwich becomes easy and also the procedure becomes safe and easy when the biological tissue M is sandwiched with respect to the second electrode member 2. It should be noted that the first electrode member 1 is described as a plate-shaped electrode member, but it is not limited only by this and it is also allowed to constitute it by a needle-shaped electrode member similarly as the second electrode member 2.

In the second electrode member 2, a portion thereof protruded from the support body 50 which is an attachment portion forms a pair of needle-shaped members 2a having circular-shapes in the section perpendicular to the axis or ring-shapes. If it is constituted by a needle-shaped electrode member, it is possible to stabilize the installation condition of the electrode members by the sticking whichever mode of biological tissue it is and the sandwich by both the electrode members becomes easy. The proximal sides of the needle-shaped members 2a are inserted into the lumens L1, L2 respectively.

A conductive wire d2 is connected to the proximal sides of the needle-shaped members 2a, and the conductive wire d2 is pulled out to the outside from a Y connector 72 and connected with the energy supply unit 20 through a coupler 77. It should be noted that the support body 50 includes a plurality of lumens and it is also allowed to constitute them by a plurality of catheters 30. And it sometimes happens that the support body 50 and the catheter 30 are generically referred to as an attachment portion.

Both the electrode members 1, 2 are arranged so as to face each other at the distal side of the support body 50 and there are applied various countermeasures for both the electrode members 1, 2 of the present embodiment so as not to be attached with a thrombus and blood even if the electric energy is applied in the blood.

To explain these countermeasures, first, it will be made clear about a state in which thrombi are to be attached to the electrode members 1, 2 which are applied with electric energy in the blood.

Figure 5:
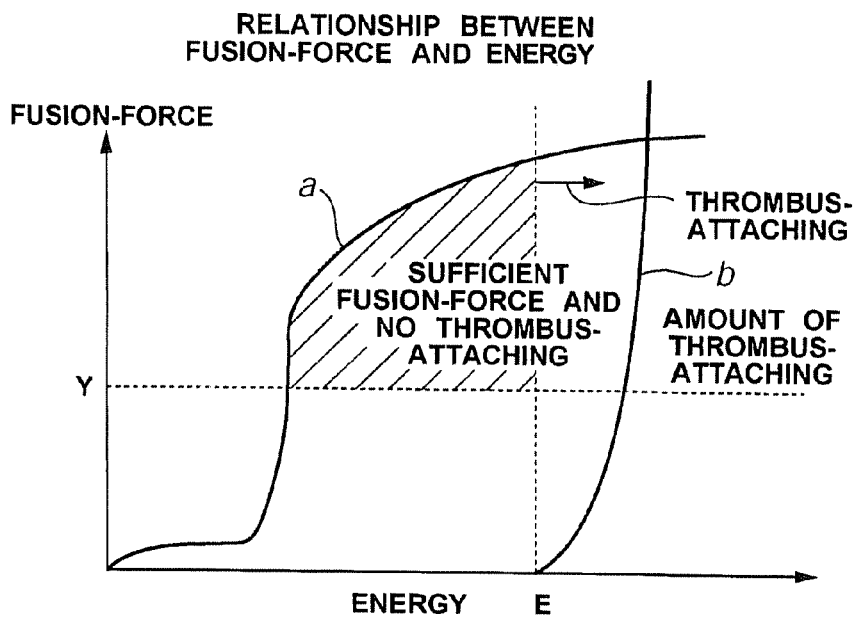
FIG. 5 is a graph showing a relationship of fusion force and electric energy.

As shown in FIG. 4, the second electrode member 2 is stuck into the foramen ovale valve M2, the first electrode member 1 is attached on the atrial septum M1 and thereafter, when electric energy is applied in a state in which the atrial septum M1 and the foramen ovale valve M2 are sandwiched by the first electrode member 1 and the second electrode member 2, generally, as shown by a solid line a in FIG. 5, fusion force of the biological tissue increases along with the increase of the electric energy and as shown by a solid line b, amount of thrombus-attaching increases radically from a certain amount of electric energy (E). Consequently, in order to obtain a fusion force (Y) of a predetermined biological tissue without being attached with the thrombus, it happens that the electric energy is to be controlled by aiming a shaded area in FIG. 5.

Figure 6:
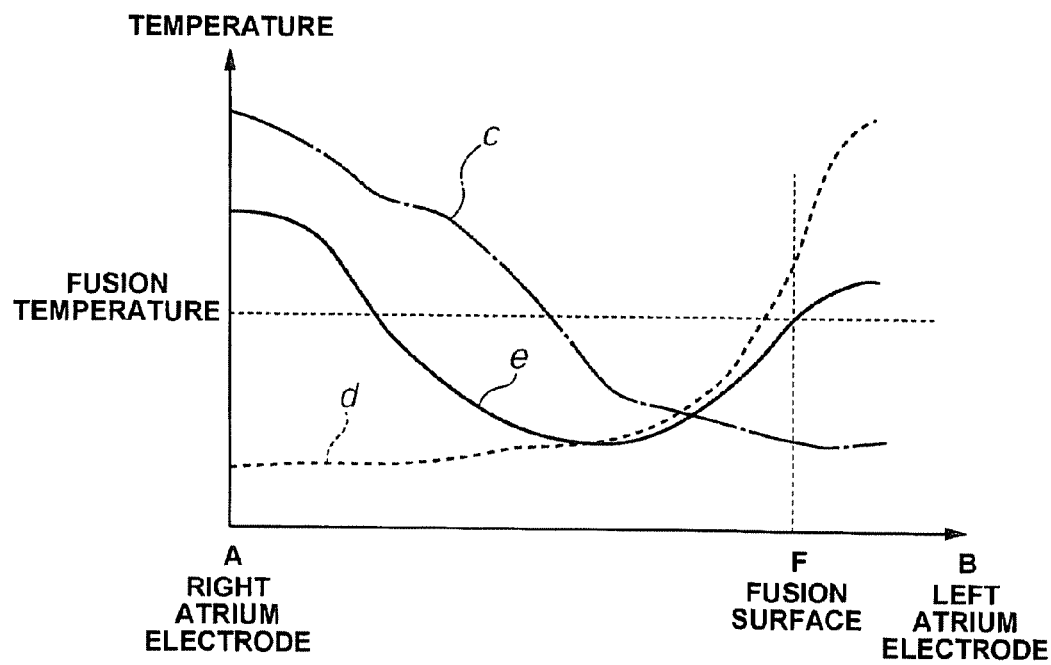
FIG. 6 is a graph showing a temperature condition in a case in which a biological tissue exists between A point corresponding to the one electrode member of FIG. 4 and B point corresponding to the other electrode member thereof.

The temperature state of each region when the electric energy is applied to the first electrode member 1 and the second electrode member 2 sandwiching the biological tissue has a tendency shown by a broken line d in FIG. 6 in a case in which the surface area of the first electrode member 1 on the right atrium side (proximal side) is larger than the surface area of the second electrode member 2 on the left atrium side (distal side) and on the contrary, in a case in which the surface area of the electrode member on the right atrium side (proximal side) is smaller than the surface area of the electrode member on the left atrium side (distal side), it will become a tendency shown by an alternate long and short dash line c. In short, it does not become a suitable temperature condition on the fusion surface between the atrial septum M1 and the foramen ovale valve M2. Therefore, in order to secure a predetermined fusion force on the fusion surface F, it is preferable to adjust the electric energy and to control the temperature such that it reaches a temperature on the fusion surface F by which the tissue is adequately fused and at the same time, such that it becomes a tendency shown by a solid line e which shows a state in which a thrombus is not attached to the second electrode member 2 on the left atrium side (distal side) either.

Consequently, a first countermeasure of the present embodiment is to adjust the electric energy which both the electrode members 1, 2 supply to the biological tissue, and more specifically, is to adjust the surface areas of the first electrode member 1 which is a plate-shaped electrode member and of the second electrode member 2 which is a pair of needle-shaped electrode members.

In particular, it is necessary for the second electrode member 2 which is a needle-shaped electrode member to have a predetermined area for the sandwiching of the biological tissue, but actually, the surface area thereof becomes smaller and the electric energy per unit area thereof becomes larger compared with those of the first electrode member 1 which is a plate-shaped electrode member and a so-called energy concentration occurs easily and also the thrombus will attach easily. Furthermore, it is positioned on the left atrium side which becomes the downstream side of the blood flow, so that there is a fear that the thrombus will stream to an undesirable position such as a peripheral vessel of a brain or the like and it is also a portion in which the thrombus-attaching must be prevented certainly.

Consequently, in the present embodiment, the first electrode member 1 is coated with an electrical insulator Z such that the surface area of the portion in which the first electrode member 1 functions as an electrode (hereinafter, referred to as "electrode area") becomes smaller than the surface area of the portion in which the second electrode member 2 functions as an electrode (hereinafter, referred to as "electrode area"), the electric energy which both the electrode members 1, 2 supply to the biological tissue is adjusted, and the electric energy concentration on one electrode member is avoided.

In short, in FIG. 3, a portion of the ventral surface side of the main body portion 1a in the first electrode member 1, which contacts the biological tissue M, is coated with the electrical insulator Z and further, the back surface side which does not contact the biological tissue M is coated with the electrical insulator Z. By constituting in this manner, the surface area of the electrode surface of the first electrode member 1 is adjusted and the thrombus-attaching with respect to the second electrode member 2 is prevented.

Here, it is possible for the electrical insulator Z coated on the back surface side of the main body portion 1a to use diamond-like-carbon (DLC), silicone, poly-ether-ethter-ketone (Peek), polycarbonate, parylene, urethane, polyetherimide, polyethersulphone (PES) and the like. These have favorable properties in electrical insulating property, heat resistance, abrasion quality, sliding property and corrosion resistance, so that they are desirably used.

In order to adjust the electric energy supply of the electrode members 1, 2, it is allowed to apply the coating also until the portion contacting with the biological tissue M with the electrical insulator Z as mentioned above and in addition, it is also allowed to adjust the surface areas of the electrode surfaces of both the electrode members 1, 2 and to coat only the side which does not contact the biological tissue of the first electrode member 1 with the electrical insulator Z. In this manner, if the portion, which does not contact the biological tissue M, of at least one of the electrode member 1 or 2 is coated with an electrical insulator, it is possible to restrict the region to which the respective electrode members 1, 2 can supply electric energy with respect to the biological tissue M, so that it does not happen that the temperature increases even for the unnecessary portions of the biological tissue M and it is possible to prevent occurrence of such a problem that a thrombus will be attached by coagulating the blood which flows in the periphery of the respective electrode members 1, 2.

Specifically, the foramen ovale valve M2 is a membrane of around 1 mm and is easily broken, and moreover, it is a portion which will receive influence of the temperature increase caused by a fact that the fine second electrode member 2 will contact therewith. On an occasion of applying treatment with respect to such a portion, when the surface areas S1, S2 of the electrode surfaces of both the electrode members 1, 2 are adjusted and the electric energy supply is adjusted, the electric energy concentration can be avoided in the respective electrode members 1, 2 and accordingly, it is possible to perform a procedure while controlling the temperature increase of the biological tissue in the vicinity of the respective electrode members without the attaching of a thrombus to any one of the electrode members and moreover without a phenomenon in which only the vicinity of either one of the electrode member sides becomes in high temperature earlier, so that it becomes possible also for the procedure to be performed more easily.

Here, on an occasion of adjustment of the electric energy supply area, it was verified by experiments about the area ratio (S1/S2) between the surface area (S2) of the electrode surface of the second electrode member 2 and the surface area (S1) of the electrode surface of the first electrode member 1.

It should be noted that the wording "surface area of electrode surface" does not include the area of the portion coated with an electrical insulator or the like for the electrode, or the area of the electrode area housed in the catheter.

For an experiment, there are prepared such first electrode member 1 and second electrode member 2 in which the surface area ratios (S1/S2) become 0.5, 0.6, 0.7, 0.8, 0.9 and 1.0. In any case, the first electrode member 1 is a plate-shaped electrode member and the second electrode member 2 is a needle-shaped electrode member. An atrial septum M1 and a foramen ovale valve M2 of a pig's heart are used and in a state in which these are soaked in the blood, the second electrode member 2 is stuck into the foramen ovale valve M2 and the first electrode member 1 is made to be a state of being contacted with the atrial septum M1, there was carried out an experiment of performing the energization by an output power of 15 W for a predetermined time period. There was obtained a result shown in the following table 1.

TABLE 1

| area ratio | thrombus-attaching to second electrode member | fusion |
|---|---|---|
| 1.0 | YES | YES |
| 0.9 | NO | YES |
| 0.8 | NO | YES |
| 0.7 | NO | YES |
| 0.6 | NO | YES |
| 0.5 | NO | NO |

As is clear from this table, the aimed fusion force was not obtained for a case in which the surface area ratio (S1/S2) is 0.5, the aimed fusion force was obtained in case of 0.6 and there existed attachment of an unfavorable thrombus in case of 1.0.

Consequently, if the area ratio (S1/S2) of the surface of both the electrode members is more than 0.6 to less than 1.0, it became clear that the thrombus attachment can be prevented and it is desirable.

Also, the experiment shows a case in which an output of the energization is 15 W, and a result shown in the following table 2 was obtained as a result after carrying out an experiment similar as the one in which the energization is performed for a predetermined time period by fixing the area ratio to be 0.7 and by changing the energization output.

TABLE 2

| Output (W) | thrombus-attaching to second electrode member | fusion |
|---|---|---|
| 10 | NO | YES |
| 15 | NO | YES |
| 20 | NO | YES |
| 30 | NO | YES |
| 50 | NO | YES |

As is clear from this table, there was no thrombus attachment to the second electrode member 2 of the left atrium in a range of 10 W to 50 W and the aimed fusion force could be obtained. Therefore, it became clear that it is enough if an output of the energization is made to be in a range of 10 W to 50 W.

The second countermeasure is such that it is made so as not to attach a thrombus even if a biological tissue is contracted by receiving the thermal influence of the respective electrode members 1, 2 and the proximal side of the respective electrode members 1, 2 is exposed.

In a case in which the procedure for inosculating the foramen ovale valve M2 and the atrial septum M1 is being executed, it may happen that there exists a portion in which the proximal side of the electrode member does not contact a living body, and also it may happen that the biological tissue is contracted by receiving the thermal influence of the respective electrode members 1, 2 and the proximal side of the respective electrode members 1, 2 which contact or stick in the biological tissue are exposed. In such an exposure, there is a fear that a thrombus attaches.

Therefore, in the present embodiment, as shown in FIGS. 3 and 4, with respect to the first electrode member 1, the region thereof of a predetermined length X1 in the direction of axial line from the end surface 50a of the support body 50 of the wire portion 1b is coated with the electrical insulator Z, and also with respect to the second electrode member 2, the region thereof of a predetermined length X2 in the direction of axial line from the support body's end surface 50a of the pair of needle-shaped members 2a is coated with the electrical insulator Z.

It is preferable that either the insulating region X1 of the first electrode member 1 and the insulating region X2 of the second electrode member 2 are made to be an exposure length which is caused at a time point when the contraction by the heating of the biological tissue M is completed. Specifically, it became clear by the experiment that it is enough if the region X (general term of X1 and X2) that the electrical insulator Z is coated is 0.5 mm to 10 mm.

As doing in this manner, when electric energy is supplied to both the electrode members 1, 2, it may not happen that the proximal side of the respective electrode members 1, 2 contacts the blood directly even if the biological tissue is contracted by receiving the thermal influence from the respective electrode members 1, 2, and the attachment of a thrombus is prevented.

With respect to even an electrical insulator Z which is used in here, it is preferable to use aforementioned diamond-like-carbon (DLC), silicone, poly-ether-ethter-ketone (Peek), polycarbonate, parylene, urethane, polyetherimide, polyethersulphone (PES) and the like.

Even in case of such electrode members 1, 2, if a coating layer C is further formed by applying coating, plating or the like on a portion which is not coated with the electrical insulator Z, that is, on a portion which is contacted with the biological tissue M by using an electrically-conductive material which is not attached with a biological tissue and a thrombus or blood, an attachment preventing effect of the tissue and the thrombus can be increased and it becomes more desirable.

As an electrically-conductive material for the coating, it is possible to use titanium nitride (TiN), titanium carbon-nitride (TiCN), chromium nitride, aluminum nitride, PTFE+nickel, PTFE+gold, platinum, silver, carbon black and the like. These have characteristics such that the tissue is not scorched; electrical conductivity is very good; abrasion quality, sliding property, corrosion resistance and heat resistance are favorable; and the like, so that they are desirable.

Figure 7:
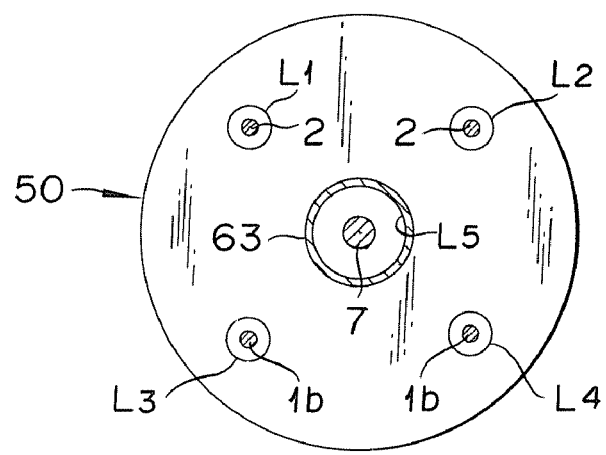
FIG. 7 is a cross-section view along line 7-7 in FIG. 2.

FIG. 7 is a cross-section view along line 7-7 in FIG. 2. The support body 50 is provided position-fixedly at the distal portion in the catheter 30 and five lumens L1 to L5 are established in the support body 50 as shown in FIG. 7, and the second electrode member 2 and the first electrode member 1 are inserted-into the first and second lumens L1, L2 and the third and fourth lumens L3, L4 as mentioned above, and the positioning hold mechanism 60 is provided in the fifth lumen L5 having the maximum aperture which exists at the center. Here, it is not always necessary for the support body 50 to be provided in a separate body with respect to the catheter 30 and it is also allowed to use the catheter 30 (multiple-lumen catheter) in which a plurality of lumens are formed inside.

The positioning hold mechanism 60, as shown in FIG. 2, generally, includes a positioning portion 61 for positioning the second electrode member 2 with respect to a foramen ovale O and a holding portion 62 for holding the foramen ovale valve M2 with respect to the sticking direction of the second electrode member 2 so as not to allow the backward movement thereof, and normally it is housed in the guiding catheter 31, but it is pushed out from the guiding catheter 31 by the operation member 7 when using it.

To describe it more in detail, there are provided in the center lumen L5 with a main tube 63 provided for reinforcing the catheter 30 and for pulling and withdrawing the positioning hold mechanism 60 in/from the catheter 30; an operation member 7 which is provided so as to move forward and backward freely in the axial direction in the main tube 63; a positioning portion 61 which is operated by the operation member 7 for the expansion and contraction thereof and which is composed of a pair of first elastic wires 66a for connecting the main tube 63 with a middle sleeve body 64; and the holding portion 62 which includes a bump member 68 provided at the distal portion of the operation member 7, a distal sleeve body 65, and a pair of second elastic wires 67 for connecting the middle sleeve body 64 with the distal sleeve body 65 and which holds the foramen ovale valve M2 by the bump member 68 and the distal sleeve body 65.

With respect to the positioning portion 61, the operation member 7 is protruded from the distal side of the main tube 63, the first elastic members 66 are displaced outward by the operation of moving the operation member 7 forward and backward in the axial direction, respective first elastic members 66 press an inner fringe of the foramen ovale O with approximately equal elastic forces, and the second electrode member 2 is center-aligned with respect to the foramen ovale O. In other words, it exhibits a function for positioning the second electrode member 2 which is positioned between both the first elastic members at the center portion of the foramen ovale O.

The holding portion 62 includes a bending mechanism W for bending the distal portion of the operation member 7 by operating the operation member 7 in the axial direction so as to move forward and backward. The bending mechanism W bends the holding portion 62 so as to face the direction in which the second electrode member 2 sticks the foramen ovale valve M2 and exhibits a function for holding the foramen ovale valve M2. Here, the bending mechanism W is constituted by the middle sleeve body 64, the distal sleeve body 65, the second elastic wire 67 for coupling both the sleeve bodies 64, 65 and the bump member 68.

The proximal tip of the first elastic wire 66 is welded on the distal tip of the main tube 63 and the distal side thereof is welded on the middle sleeve body 64. On the other hand, the proximal tip of the second elastic wire 67 is welded on the distal tip of the middle sleeve body 64 and the distal side thereof is welded on the distal sleeve body 65.

It is preferable for a specific example of the first and second elastic wires 66, 67 to use a metallic wire such as stainless steel, nickel-titanium, super elastic alloy (for example, Ni—Ti alloy) and the like with an outer diameter of around 0.1 mm to 0.5 mm. It is also allowed to prevent the tissue from being wounded by coating a metallic wire with a (soft) resin tube.

The holding portion 62 has a constitution in which the first elastic wire 66 of the proximal side bends prior to the second elastic wire 67 of the distal side; the positioning of the second electrode member 2 is executed; subsequently, the operation member 7 itself is deformed accompanied by the bump member 68 and the distal sleeve body 65; and the positioning portion 61 holds the foramen ovale valve M2 after positioning the second electrode member 2.

For such a constitution, for example, it is also possible to use such methods as a method which uses the second elastic wire 67 having higher stiffness materially than that of the first elastic wire 66; and a method in which an easily-deformable portion is formed by bending a portion of the first elastic wire 66 beforehand or the like and when traction force is applied, the first elastic wire 66 is bent previously compared with the second elastic wire 67 by the deformation of the easily-deformable portion.

When doing in this manner, the first elastic wire 66 of the proximal side is attached to an inner fringe of the foramen ovale O only by the traction of the operation member 7 backward and the positioning of the second electrode member 2 can be executed, and when applying further traction, the second elastic wire 67 of the distal side is protruded and deformed like an arc shape toward the outward direction in the radial direction and it is possible to hold the foramen ovale valve M2 so as not to allow the backward movement thereof such that it becomes easy for the second electrode member 2 to be stuck.

Figure 8:
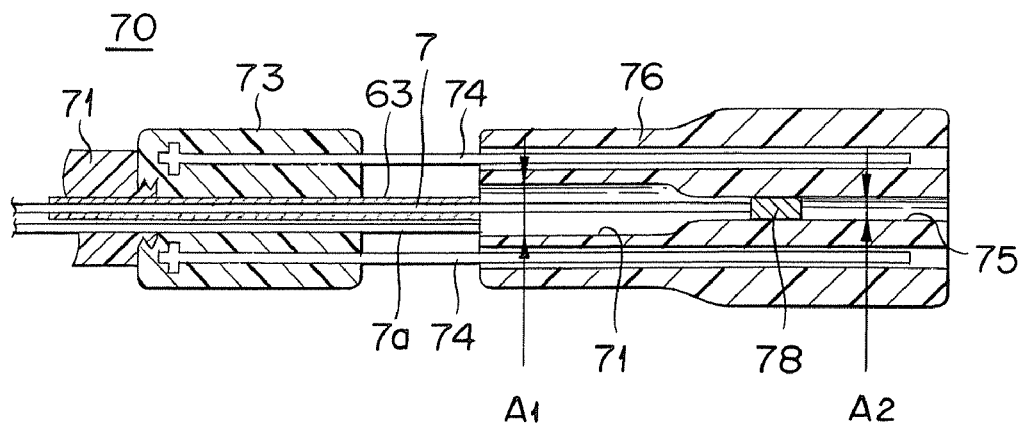
FIG. 8 is a cross-section plan view of an operation unit at hand of the medical device.

FIG. 8 is a cross-section plan view of an operation unit at hand of the medical device. With respect to the operation unit at hand 70, as shown in FIG. 8, there are generally included a first operation body 73 with which the proximal tip of the catheter 30 is coupled through a coupling member 71 and a Y connector 72 and a second operation body 76 approachable and separable with respect to the first operation body 73 by sliding along slide rails 74 in which there is established a through-hole 75 into which the pair of slide rails 74 protruded from the rear end side of the first operation body 73 are inserted.

The main tube 63 is inserted into the inside of the first operation body 73 and the rear end thereof is coupled to the distal tip of the second operation body 76. Consequently, when applying backward traction on the second operation body 76, it is possible to withdraw the whole positioning hold mechanism 60 within the center lumen L5 of the catheter 30. It should be noted for the material constituting this main tube 63 that it is possible to use a deformable elastic material such as, for example, polyimide resin, polyurethane, PET, nylon, fluorine resin, polypropylene and the like. In addition, it is also allowed to make the operation unit at hand 70 as a metallic pipe and to couple it with the main tube 63 of an elastic material.

With respect to the operation member 7, the proximal tip thereof is mounted on a knob 78 which slides reciprocatingly in a slide groove 75 formed in the center of the second operation body 76 and when sliding the knob 78 reciprocatingly in the slide groove 75, the whole operation member 7 moves reciprocatingly in the main tube 63. The operation member 7$a$ is a member for moving the first electrode member 1 forward and backward, and according to the present embodiment, the proximal side thereof is coupled to the distal portion of the second operation body 76.

The slide groove 75 is formed, as shown in FIG. 8, to be broader for the width A1 of the front half portion than the width A2 of the rear half portion and thus, in a case in which the knob 78 is positioned at the front half of the slide groove 75, it is possible to move the knob 78 in a tilting manner in a direction perpendicular to an axial line of the slide groove 75 and thus, it is possible to rotate the operation member 7 in the catheter 30 centering around the axial line and to adjust the distal tip position rotatingly. Consequently, when the operation member 7 is operated by operating the knob 78 according to the operation unit at hand 70, it is possible to adjust not only the position in forward and backward direction but also the rotational position and the convenience of the procedure for the inserting to the left atrium is improved considerably.

The energy supply unit 20 is such an electrical unit mentioned above and it is possible for the energy supply method to use such a method as a monopolar system in which the second electrode member 2 on the left atrium L side is made to be an active electrode and is energized with respect to a counterpart electrode plate provided at the back portion, a monopolar system in which the first electrode member 1 on the right atrium R side and the second electrode member 2 on the left atrium L side are made to be active electrodes and are energized with respect to counterpart electrode plates provided at the back portion, a bipolar system in which energization is executed between the first electrode member 1 on the right atrium R side and the second electrode member 2 on the left atrium L side and the like. In particular, if it is formed as a bipolar system for controlling the current by the impedance of the biological tissue between the first electrode member 1 and the second electrode member 2, there are advantages that it can have correspondence easily in response to the state of the tissues of the foramen ovale valve M2 and the atrial septum M1 which differ depending on a person and the safety and the convenience of the procedure are obtained.

A power supply unit 20A is constituted by a power supply, a control unit for controlling current and the like and a well-known system constitution is employed, so that the explanation thereof will be omitted. Here, it is not necessary to employ a direct-current power supply for the power supply and it is also allowed to employ an alternative-current power supply.

Next, the operation of the present embodiment will be explained.

FIG. 9A to FIG. 9D are schematic views showing operation states of the medical device. It should be noted in the drawings that the shape and the position of the second elastic wire member 66 have a state of approximately the same plane as those of the first electrode member 1 and the second electrode member 2, but in order to facilitate understanding, the drawn position thereof is shown in a state being displaced by 90° and is different from the actual deformed state.

First, the surgery operator moves the second operation body 76 of the operation unit at hand 70 backward with respect to the first operation body 73 and makes a state in which the first electrode member 1, the second electrode member 2 and the like are housed in the guiding catheter 31, and in this state, based on the common procedure, the distal tip of the guiding catheter 31 is inserted from a predetermined position of the living body by making a guide wire as a guide thereof and it is reached until the right atrium R by passing through the inferior vena cave J. Here, it is also allowed to insert only the guiding catheter 31 into the living body and afterward to insert the catheter 30 by making that guiding catheter 31 as a guide.

Figure 9A:
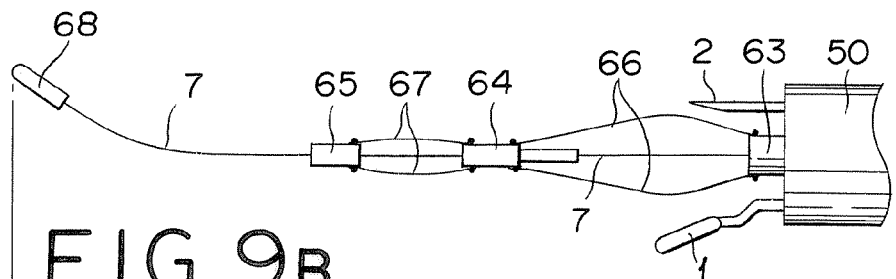
FIG. 9A to FIG. 9D are schematic views showing operation states of the medical device.

Next, the first operation body 73 is operated and the distal tip of the catheter 30 is protruded to the left atrium L from the right atrium R through the foramen ovale O and thereafter, the knob 78 is moved forward and, as shown in FIG. 9A, the distal tip of the operation member 7 is protruded from the distal sleeve body 65 and inserted into the left atrium L. It is possible to observe this protruding state from the outside by eyes if a marker is provided on the bump member 68 or the like, and it is possible to sensuously identify a place in which the distal tip of the operation member 7 is positioned when the distal tip of the operation member 7 is bumped with an inner wall of the left atrium L or the like according to this protrusion even in a case in which it is difficult to observe by eyes, so that the convenience is improved. It should be noted that the knob 78 is positioned at a wide front half portion of the slide groove 75 and when this is moved in a tilting manner, the identification of the distal position becomes easy sensitively.

Figure 9B:
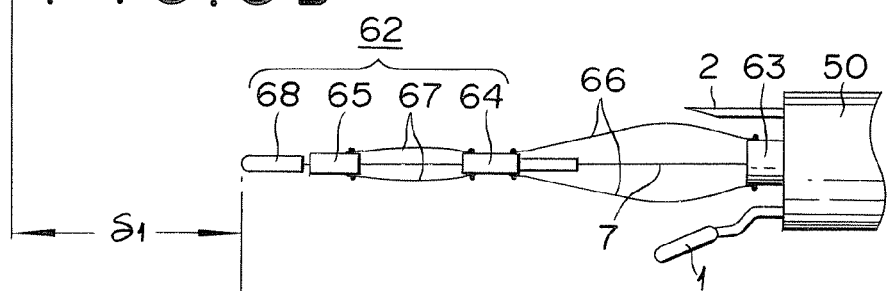

After the identification of the distal position of the operation member 7, as shown in FIG. 9B, the knob 78 is moved backward until the bump member 68 of the operation member 7 attaches to the distal sleeve body 65 (amount of backward movement is ⌈δ1⌋ in FIG. 9B). Then, the first operation body 73 is operated, and the second elastic wire 67, the first electrode member 1 and the second electrode member 2 are positioned in the vicinity of the foramen ovale valve M2 and the whole holding portion 62 is inserted into the left atrium L side.

Figure 9C:
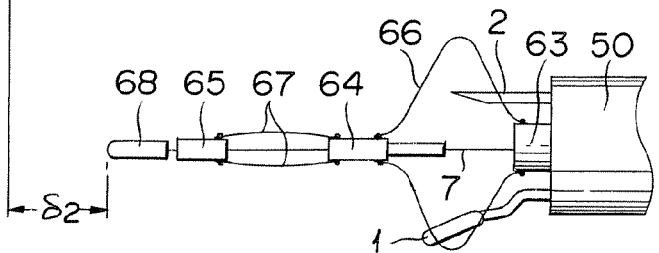

When the knob 78 is further moved backward (amount of backward movement is ⌈δ2⌋ in FIG. 9C), the operation force for the backward movement is transmitted by the operation member 7 to the first elastic wire 66 firmly fixed on the distal tip of the main tube 63 through the bump member 68, the distal sleeve body 65, the second elastic wire 67 and the middle sleeve body 64, and the first elastic wire 66 is, as shown in FIG. 9C, protruded and deformed in an arc shape toward the outside direction in the radial direction. However, at this time point, the second elastic wire 67 is not deformed.

Consequently, it happens that the first elastic wire 66 is deformed while pushing and widening an opening edge portion of the foramen ovale O, so that the second electrode member 2 which is provided in close vicinity of the first elastic wire 66 is center-aligned with respect to the foramen ovale O and the second electrode member 2 is positioned at the center of the foramen ovale O.

Figure 9D:
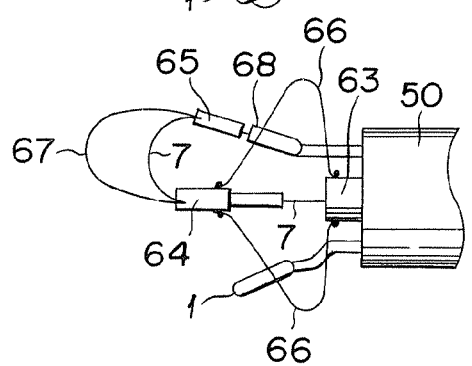

Further, when the knob 78 is operated so as to move backward until a rear end of the middle sleeve body 64 is attached to the distal tip of the main tube 63, as shown in FIG. 9D, the first elastic wire 66 is not deformed so much and the second elastic wire 67 of the distal side is protruded and deformed in an arc shape toward the outside direction in the radial direction by the operation force. Consequently, in the left atrium L, the bump member 68 and the distal sleeve body 65 approach to the second electrode member 2, so that the bump member 68 and the distal sleeve body 65 are attached to the surface of the left atrium side of the foramen ovale valve M2 and hold this.

In this state, the first operation body 73 is moved forward and the second electrode member 2 which is provided at the distal tip of the catheter 30 is stuck at a predetermined position of the foramen ovale valve M2. The sticking state is a state shown in FIG. 1 and there exist the atrial septum M1 and the foramen ovale valve M2 between the first electrode member 1 and the second electrode member 2.

When the sticking is executed once, the position of the second electrode member 2 becomes fixed in relation with the foramen ovale valve M2, so that in this step, the second operation body 76 is returned once and, as shown in FIG. 9B, the first elastic wire 66 and the second elastic wire 67 are made to be in a straight-line shape and thereafter, the second operation body 76 is operated so as to move backward and the whole positioning hold mechanism 60 is withdrawn in the lumen L5 of the catheter 30 by the main tube 63.

On the occasion of this withdrawal, also the operation member 7a of the first electrode member 1 coupled to the second operation body 76 moves backward along the lumen of the catheter 30, so that a bend portion f of the first electrode member 1 is deformed so as to approach the second electrode member 2 side by an end portion of the catheter 30 and, the atrial septum M1 and the foramen ovale valve M2 are strongly sandwiched between both the electrode members 1, 2.

When electric current of 15 to 50 W is flown between the first electrode member 1 and the second electrode member 2 while maintaining this sandwich state, it is possible to supply electric energy to the biological tissue from the electrode surfaces of the respective electrode members 1, 2 which were made to have predetermined surface areas by the electrical insulator Z and it happens that the biological tissue M in the vicinity of or in contact with the respective electrode members 1, 2 will be equally heated.

Also, the electric energy is controlled such that a thrombus caused by a phenomenon that the blood flowing at the periphery of the respective electrode members 1, 2 coagulates is not generated, so that even if a portion of both the electrode members 1, 2 is exposed in the blood, it never happens that the thrombus is attached to that portion. Moreover, owing to a fact that the surfaces of the electrode members are plated, the attachment of the thrombus to the respective electrode members is prevented more certainly.

By doing in this manner, when heating until a state in which both the tissues of the atrial septum M1 and the foramen ovale valve M2 are fused, the foramen ovale valve M2 and the atrial septum M1 start contracting and a portion of the first electrode member 1 and the second electrode member 2 is exposed in the blood. However, with respect to the first electrode member 1 and the second electrode member 2, the regions X1, X2 of a predetermined length in the axial line from the support body 50 thereof are coated by the electric insulation member Z, so that it becomes hard for this exposed portion to be attached with the thrombus.

Then, when the heating is continued while maintaining a fusion temperature, the tissues of the atrial septum M1 and the foramen ovale valve M2 melt and are fused mutually by an adhesive agent such as collagen, erastin and the like.

When the fusion is completed, the energization is stopped, the first operation body 73 is moved backward, also the first electrode member 1 and the second electrode member 2 which are located at the distal tip of the catheter 30 are housed in the guiding catheter 31 together with the positioning hold mechanism 60, and the guiding catheter 31 is pulled out from the living body. It should be noted that a very small hole remains on the foramen ovale valve M2 by the pulling-out of the first electrode member 1, but it is healed afterward and bad influence such as generation of a thrombus or the like will never occur.

<Second Embodiment>

Figure 10:
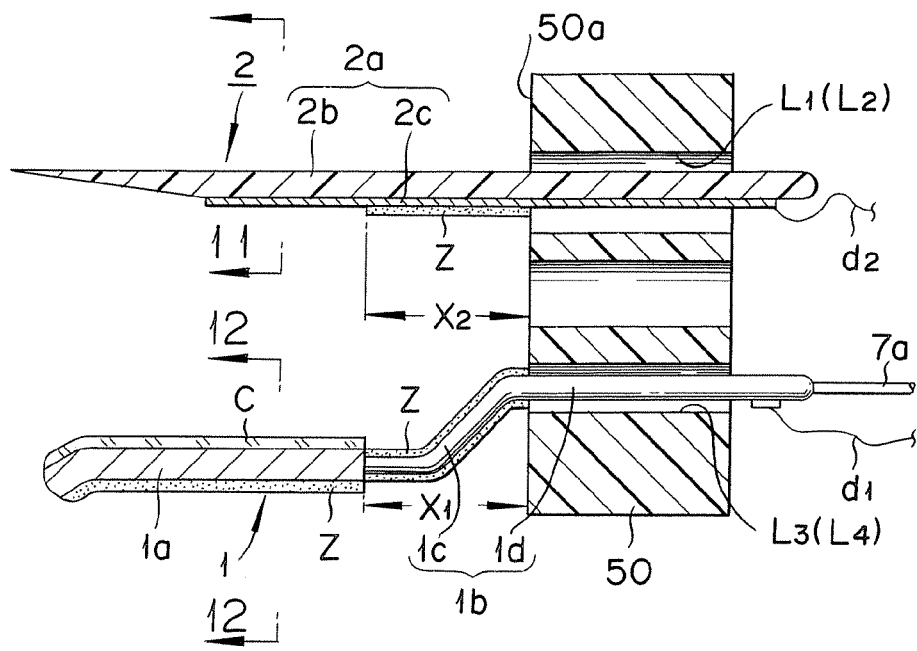
FIG. 10 is a cross-section view showing a clamper according to a second embodiment of the present invention.
Figure 11A:
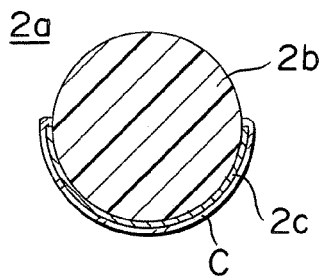
FIG. 11A is a cross-section view along line 11-11 in FIG. 10.
Figure 11B:
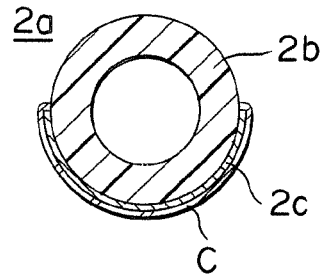
FIG. 11B is a cross-section view showing a modified example of a second electrode member.
Figure 12:
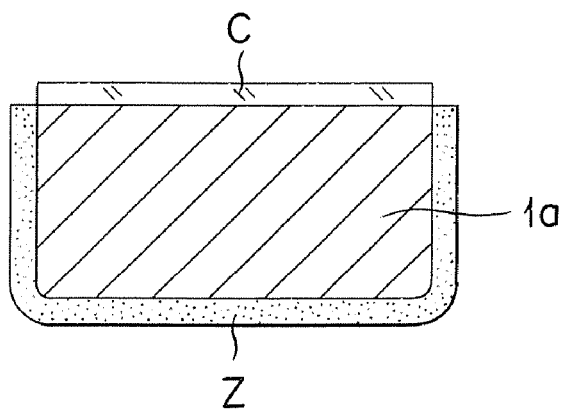
FIG. 12 is a cross-section view along line 12-12 line in FIG. 10.

FIG. 10 is a cross-section view showing a clamper according to a second exemplified embodiment of the invention, FIG. 11A is a cross-section view along a 11-11 line of the FIG. 10, FIG. 11B is a cross-section view showing a modified example of the second electrode member and FIG. 12 is a cross-section view along a 12-12 line of the FIG. 10. It should be noted in the drawings that the same numerals are given to the same ones as the constitution members for the first exemplified embodiment.

As a third countermeasure for preventing a problem that a thrombus will be attached to the electrode member, it is also allowed to not transfer joule-heat of an electrode portion in the time of the electric energy supply to the side that a biological tissue does not contact.

The second electrode member 2 of the first exemplified embodiment is composed of a portion thereof which is protruded from a support body 50 on an attachment portion is a circular-shaped in the section perpendicular to the axis or a ring-shaped pair of needle-shaped members 2a, but when the whole needle-shaped member 2a is formed by a metallic material, for example, a SUS material or the like and when the electric energy is supplied, the whole becomes a substantially uniform temperature and even a portion which is not contacted with a biological tissue or a portion which is exposed in the blood becomes high temperature, so that there is a fear that a thrombus is attached to this portion.

Consequently, the needle-shaped member 2a of the present exemplified embodiment is, as shown in FIG. 10, constituted for the main body portion 2b thereof by a synthetic resin which has heat resistance and also electrical insulating property, and there is provided at a partial outside circumferential surface of the main body portion 2b with an electrically-conductive film 2c so as to extend in the direction of an axial line and it is constituted such that the joule-heat generated at the electrically-conductive film 2c is prevented from being transferred to the anti-electrically-conductive film side.

More specifically, the electrode members 1, 2 of the first exemplified embodiment is constituted for the main body thereof by an electrically-conductive member and the circumferential surface thereof is coated with an electric insulation member, but the electrode members 1, 2 of the present exemplified embodiment is, on the contrary, constituted for the main body thereof by an electric insulation member such as a synthetic resin and the like and the circumferential surface thereof is coated with an electrically-conductive member.

Here, it is preferable, similarly as the first exemplified embodiment, to form the ventral surface side by which the main body portion 1a of the first electrode member 1 contacts with the biological tissue M and a portion in which the electrically-conductive film 2c of the second electrode member 2 is provided with predetermined surface areas of electrode surfaces so as to adjust the electric energy supply.

The needle-shaped member 2a is allowed to be formed by either of solid and hollow cylinders, as shown in FIGS. 11A and 11B, and it is preferable to employ a constitution in which the electrically-conductive film 2c is provided on the surface side facing the first electrode member 1 and the electric energy is supplied certainly to the biological tissue M.

It is preferable for the electrically-conductive film 2c to use a SUS material, gold, silver, platinum, tungsten, palladium or alloys of these, Ni—Ti alloy, titanium alloy or the like.

Also, it is allowed for the synthetic resin which constitutes the main body portion 2b if it is a material having an electrical insulating property, low thermal conductivity, heat resistance, abrasion quality and sliding property and, for example, it is preferable to use such as poly-ether-ethter-ketone (Peek), polycarbonate, polyetherimide, urethane, poly-para-xy-lylene, silicone, polyethersulphone (PES) and the like.

Even in a case of a needle-shaped member 2a having the electrically-conductive film 2c, it is also allowed to apply coating by the electrical insulator Z to the region of a predetermined length X2 in the direction of axial line from the support body's end surface 50a, as in the first exemplified embodiment, in consideration of the thermal contraction of the biological tissue M. With respect to the second electrode member 2, it is also allowed to apply coating by the electrical insulator Z to the wire portion 1b within the region of a predetermined length X1 in the direction of axial line from the end surface 50a of the support body 50. It is preferable for the regions X1, X2 which are insulated to be determined in consideration of the amount of shortening of the biological tissue M, that is, the exposed length, which occurs at a time point when the procedure is completed and specifically, a fact that it will be 0.5 mm to 10 mm is similar as that of the former exemplified embodiment.

Even in case of such electrode members 1, 2, if a coating layer C is further formed by applying coating, plating or the like on a portion which is not coated with the electrical insulator Z, that is, on a portion which is contacted with the biological tissue M by using an electrically-conductive material which is not attached with a biological tissue, a thrombus or blood, an attachment preventing effect of the tissue and the thrombus can be increased and it becomes more desirable. It should be noted that an electrically-conductive material for the coating layer C is similar as the coating material of the former exemplified embodiment.

Figure 13:
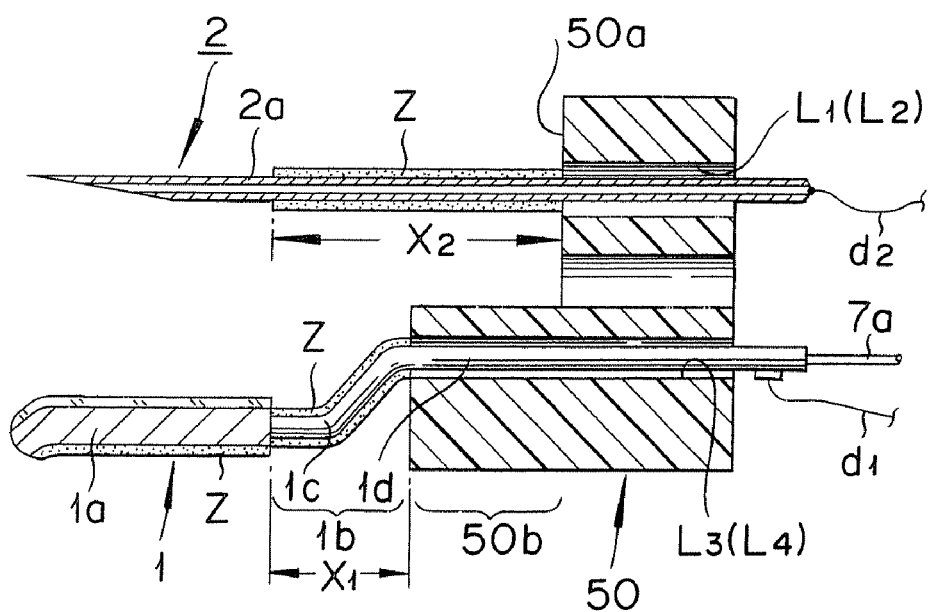
FIG. 13 is a cross-section view showing a clamper according to another exemplified embodiment.

The present invention is not limited only by aforementioned exemplified embodiments and it is possible for a person skilled in the art to employ various modifications within the technical concept of the present invention. For example, the clamper K of the exemplified embodiment is such that the first electrode member 1 and the second electrode member 2 directly protrude from the support body 50, but it is not limited only by this and it is allowed, as shown in FIG. 13, to employ a constitution in which an electrical insulation portion 50b is protrudingly provided on a lower half portion of the end surface of the support body 50 and the first electrode member 1 is protruded from the electrical insulation portion 50b. The electrical insulation portion 50b is formed by using the same material as the catheter 30 in the present embodiment, so that the electrical insulation portion 50b itself has elasticity to a certain degree and the work region in which the first electrode member 1 approaches and separates with respect to the second electrode member 2 is expanded and the procedure will be performed more easily. Moreover, the region X which is coated with the electrical insulator Z can be smaller as much as the length with which the electrical insulation portion 50b is protrudingly provided, so that it becomes advantageous also on the manufacturing aspect.

In the exemplified embodiment, both the electrode members are coated with the electrical insulator Z, but it is also possible, depending on the lesion portion, to use members in which only the proximal side of either one of the electrodes is coated with the electrical insulator Z, so that it is also allowed to apply the coating of the electrical insulator Z only for one of them.

In the exemplified embodiment, it was explained with respect to a device which is used in a treatment for closing a defect of PFO, but the invention is not limited only by this and it is possible to use it in case of closing a passway-shaped defect such as a left auricle closing device (Left Atrial Appendage) or in case of thermally necrosing a biological tissue in a predetermined region.

With respect to the PFO closing device of aforesaid embodiment, it is merely housed in the catheter and operates a sandwich mechanism by the operation member, but it is not limited only by this and, for example, it is also possible to carry it until a predetermined position by employing a combination with a so-called catheter having a balloon.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A medical device for fusing two biological tissues, comprising:
   a first electrode member and a second electrode member protruded from a non-electrically-conductive attachment portion configured to sandwich the biological tissues; and
   an energy supply unit configured to supply electric energy to the first electrode member and the second electrode member,
   wherein the first electrode member is configured to contact one side surface of one of the tissues, the second electrode member is configured to stick in the other tissue, a region of a predetermined length in a direction of axial line from the attachment portion in at least one of the electrode members within the first electrode member and the second electrode member is coated with an electrical insulator, and an area ratio (S1/S2) between surface area (S1) of the first electrode member and surface area (S2) of the second electrode is made to be more than 0.6 to less than 1.0,
   wherein surface area (S1) and surface area (S2) exclude the region in at least one of the electrode members that is coated with the electrical insulator such that surface area (S1) defines the entire conductive electrode surface of the first electrode member and surface area (S2) defines the entire conductive electrode surface of the second electrode member.

2. The medical device according to claim 1, wherein the region coated with the electrical insulator is configured to be a region in which contraction of the biological tissues is completed by the electric energy supply.

3. The medical device according to claim 1, wherein the region coated with the electrical insulator is configured to be 0.5 mm to 10 mm in a direction of axial line from the attachment portion.

4. The medical device according to claim 1, wherein the first electrode member and the second electrode member are coated with an electrically-conductive material which is hard to be attached with both the biological tissues, a thrombus or blood for the surfaces thereof which are not coated with the electrical insulator.

5. The medical device according to claim 1, wherein the second electrode member comprises a portion thereof which is protruded from the attachment portion and is constituted by a pair of needle-shaped members with a circular-shaped or ring-shaped cross-section perpendicular to the axis.

6. The medical device according to claim 5, wherein the medical device includes a positioning hold mechanism composed of a positioning portion for positioning the second electrode member with respect to the foramen ovale and a holding portion for holding a foramen ovale valve so as not to allow the backward movement thereof with respect to the sticking direction of the second electrode member.

7. The medical device according to claim 1, wherein the first electrode member is formed for a portion thereof which is protruded from the attachment portion to be a flat plate shape so as to face the second electrode member.

8. The medical device according to claim 1, wherein at least one of the both electrode members comprises a main body composed of a synthetic resin and an electrically-conductive film is provided at a partial outside circumferential surface of the main body.

9. The medical device according to claim 8, wherein the main body comprises a synthetic resin which has at least heat resistance or electrical insulating property.

10. The medical device according to claim 8, wherein there is provided the electrically-conductive film so as to extend in the direction of axial line at the opposing surface sides of the both electrode members which are provided by facing each other.

11. The medical device according to claim 8, wherein the electrically-conductive film is coated so as to adjust the electric energy supply of the each electrode member.

12. The medical device according to claim 8, wherein the surface of the electrically-conductive film is coated with an electrically-conductive material which is hard to be attached with the biological tissues, a thrombus or blood.

13. The medical device according to claim 1, wherein the attachment portion is constituted by a catheter provided in a guiding catheter.

14. The medical device according to claim 1, wherein the medical device includes a positioning mechanism for positioning the second electrode member at a predetermined position with respect to a foramen ovale.

15. The medical device according to claim 1, wherein the energy supply unit controls electric current by impedance of the biological tissues between both the electrode members.

* * * * *